United States Patent [19]
Yoshida

[11] 4,197,290
[45] Apr. 8, 1980

[54] VACCINE

[76] Inventor: Kosaku Yoshida, 2095, Sugao, Takatu-ku, Kawasaki, Kanegawa-ken 213, Japan

[21] Appl. No.: 947,103

[22] Filed: Sep. 29, 1978

[30] Foreign Application Priority Data

Sep. 30, 1977 [JP] Japan ................................ 52/118426

[51] Int. Cl.$^2$ ............................................. A61K 39/02
[52] U.S. Cl. .................................................... 424/92
[58] Field of Search ........................................... 424/92

[56] References Cited

PUBLICATIONS

C.A. 80 #143891d, (1974), 80 #13560j, (1974), 83 #145584s, (1975), 83 #145636k, (1975), 83 #156579b, (1975), 83 #39104a, (1975), 87 #50108b, (1977), 76 #57636k (1972), 76 #44572m, (1972).

*Primary Examiner*—Shep K. Rose
*Attorney, Agent, or Firm*—Newton, Hopkins & Ormsby

[57] ABSTRACT

A vaccine effective against challenge infections, such as bovine mastitis is prepared from *Staphyloccus aureus* or *Staphylococcus epidermidis* strain.

8 Claims, No Drawings

VACCINE

BACKGROUND OF THE INVENTION

This invention is related to application Ser. No. 195,474, filed Nov. 3, 1971, now abandoned.

1. Field of the Invention

This invention relates a method of producing a vaccine for the prevention and treatment of bovine mastitis.

2. Description of the Prior Art

In the prior art it is known to extract a polysaccharide which is called Smith Surface Antigen (SSA) or Staphylococcal Polysaccharide Antigen (SPA) from the Smith-diffuse strain of *Straphyloccus aureus* (*S. aureus*), the reagent of SSA or SPA inducing protection in animals against challenge infection with *S. aureus* strains. The protection induced thereby, however, is specific for the Smith-diffuse or Smith-diffuse-like strains. The Smith-diffuse or Smith-diffuse-like strains are also regarded as single types of encapsulated organisms, including Wiley's capsule type strains which are identical to the Smith-diffuse or Smith-diffuse-like strains.

In the prior art, the extraction of polysaccharide from the capsules of *S. aureus* strains is required to be carried out using the Smith-diffuse strain, since encapsulated *S. aureus* strains, other than the Smith-diffuse of Smith-diffuse-like organisms, have not heretofore been isolated.

It is known that the thus extracted reagents are not effective in the prevention of bovine mastitis.

SUMMARY OF THE INVENTION

It is an object of this invention to provide a method of extracting polysaccharide from encapsulated Staphyloccus strains for the purpose of providing a vaccine for the prevention and treatment of bovine Staphylococcal mastitis.

This and other objects of this invention as will hereinafter become clearer by the following description have been attained by immunizing bovine herds with a vaccine comprising a capsular polysaccharide substance derived from encapsulated strains.

DESCRIPTION OF THE PREFERRED EMBODIMENTS

Generally, unencapsulated *S. aureus* strains produce a compact type colonial morphology in the serum soft sugar (SSA) which consist of, e.g., Brains Heart Infusion (BHI) media, agar and normal rabbit sera, while encapsulated *S. aureus* strains represent diffuse type growth therein. However, diffuse type of encapsulated strains convert their colonial morphology to compact type growth in the SSA containing homologous strain antisera, but, do not convert their growth type with heterologous strain antisera. Any diffuse type of encapsulated *S. aureus* strains which exhibit compact type colonial morphology in the SSA containing anti-Smith-diffuse strain sera will hereinafter be designated as type A. A second strain which produce diffuse type colonial morphology in the SSA containing anti-type A sera, however, produce compact type colonial morphology only in the SSA containing homologous antisera, the second strains being designated as type B. A third strain which produce diffuse colonies in the SSA containing anti-type A and/or anti-type B sera, however, produce compact type colonial morphology only in the SSA containing homologous antisera, the third strain is herein designated as type C. Similarly, types D, E, F and so on, are designated. Using these serologically different capsular type strains of *S. aureus*, capsular polysaccharides are extracted as follows. The organisms grown on Modified 110 media, which is described later, are treated with sonic oscillator to obtain capsular material, then, cells are removed by centrifugation therefrom. From the cell surface and capsular fraction, nucleic acids, proteins and lipids are removed by using ribonuclease, deoxyribonuclease, chloroform containing butanol, acetone and ether. Polysaccharides thus obtained induce protection in animals against challenge infection with homologous encapsulated strains.

Generally, strains of *S. epidermidis* have been considered as avirulent to both animals and humans. Recently, however, infections caused by these strains have become a problem, although the pathogenic factor causing these infections remains unknown.

After numerous experiments the significance of the capsule for the establishment of infections with encapsulated strains of *S. epidermidis* has now been recognized which had previously not been reported. Capsular polysaccharide obtained from encapsulated strains of *S. epidermidis* has been found effective as a vaccine for active immunization against Staphylococcal infections.

It should be noted that passive immunization of mice with hyperimmune rabbit serum prepared with strain ATCC 31432 (SMU 76) of *S. epidermidis*, which was isolated by this investigator, is capable of protecting against challenge by homologous strains. Also, passive protection activity of this rabbit immune serum could be absorbed out with the addition of strain SMU 76. When strains of *S. epidermidis* exhibiting mouse virulence also exhibit activity, such as the ability to absorb the passive protective activity of rabbit anti SMU 76 strain, they can be regarded as encapsulated strains of *S. epidermidis*.

The encapsulated strain of *S. epidermidis* may be isolated from a culture of *S. epidermidis* strains in brain heart infusion broth, or in such other broths as No. 110 broth.

The culture can be obtained by culturing said broth at from 20° C. to 40° C., preferably from 26° C. to 37° C. The organisms are then isolated by centrifuging, preferably at about 7000×g. The centrifuging is conducted for from 10 minutes to one hour, preferably, 20 minutes. The organisms may be washed with sterile physiological saline solution if desired. The organisms so recovered are then tested for virulent activity by suspending the organisms in physiological saline and the turbidity adjusted to 1.0 o.d. spectrophotometrically at 430 mµ. The cell suspension is then diluted at 1:10 in accordance with the plate count method with physiological saline. Five tenths ml (0.5 ml) of it is injected intraperitoneally into 5 mice weighing approximately 15 gms. When more than 4 mice are killed within 7 days after the injection with *S. epidermidis* strains, these strains are tentatively designated as mouse virulent.

It is the virulent strain of *S. epidermidis* which are useful in the preparation of vaccine of this invention. In particular ATCC 31432 (SMU 76) strain of *S. epidermidis* has been found particularly effective as a vaccine source.

A heat-killed vaccine may be prepared by preparing a cell suspension from the organisms prepared as described previously in a physiological saline. The temperature of the kill is not critical so long as it is sufficient to kill the organism. Heating to temperatures of about 121° C. for about 15 minutes has proven satisfactory.

The heat-killed vaccine may be used directly for an active immunization or it may be used to prepare a vaccine for a passive immunization through the use of an appropriate host animal such as a rabbit from which a hyperimmune serum may be obtained by known procedures. It is preferred to employ the strain ATCC 31432 (SMU 76) of *S. epidermidis* to prepare the vaccine for either active or passive immunization. The structure of this particular strain has been demonstrated by electronmicroscopy.

A particularly preferred vaccine comprises the capsular polysaccharide associated with the encapsulated *S. epidermidis*. The polysaccharide may be obtained by culturing the cells in a suitable medium such as Modified 110 or brain heart broth followed by sonic oscillation and centrifuging. The capsular polysaccharides are contained in the supernatant phase and are recovered.

The dosage of vaccine given to the animal to be protected is sufficient to yield the desired antibody response. Generally, dosages of from 0.0066 mg/gm to 0.66 mg/gm of body weight have proven adequate. Periodic injections with the vaccine are necessary to maintain the necessary antibody levels. The vaccine may be given to the animal as necessary to induce a suitable antibody response. These injections may be weekly, bi-weekly, monthly, or even less often, provided the desired antibody level is maintained in the animal. With cows, dosages of about 0.07 mg to 0.11 mg/kg have proven effective when given twice with 14 days intervening. The preferred vaccine is the capsular polysaccharide obtained by culturing ATCC 31432 *S. epidermidis* or *S. aureus*, strains A and B.

Having generally described the invention, a more complete understanding can be obtained by reference to certain specific examples, which are included for purposes of illustration only and are not intended to be limiting unless otherwise specified.

EXAMPLES

Example 1

A Smith-diffuse strain was cultivated at 37° C. for overnight in the BHI media. The organisms, then, were harvested by centrifugation at 7,000×g for 20 minutes and suspended in 0.85% of NaCl solution after washing once with 0.85% NaCl solution by centrifugation. The turbidity of this bacterial suspension was adjusted to 1.0 in O.D. at 430 m$\mu$ and was autoclaved at 121° C. for 15 minutes to produce a "heat-killed" vaccine. One to 1.5 ml of the heat-killed vaccine was injected intravenously into a rabbit via ear vein three successive days for three weeks. Ten days after the final injection, blood was taken from the rabbit, and the sera was separated therefrom. However, when the serum titer was insufficient, booster injections were given. The antisera activity was titrated as follows. Test sera was filtered using a membrane filter having a pore size of less than 0.6$\mu$. The sera was diluted in a two-hold dilution system, 1:2 to 1:28, with 0.85% NaCl solution. The Smith-diffuse strain was cultured in the BHI broth at 37° C. for overnight, then, diluted $10^{-6}$ with sterile 0.85% NaCl solution. One tenth ml of the above diluted antisera and 0.1 ml of diluted bacterial suspension were poured into sterile test tubes, and then, 10 ml of the BHI containing 0.15% agar, which was maintained at 45° to 50° C. after autoclaving at 121° C. for 15 minutes, was added thereto.

The test tubes were maintained at 4° C. for 30 to 60 minutes to solidify the media. Thereafter, these tubes were incubated at 37° C. and colonial morphologies were determined after 18 to 24 hours. Then, the strain produced compact to diffuse colonies in the SSA depending upon the antisera concentration. In this test, maximum antisera dilution producing compact type colonial morphology was made as 1 unit and 2 units/0.1 ml of antisera was used for the further testings. When unknown strains, encapsulated and diffuse type *S. aureus*, produce compact type growth in the SSA containing anti-Smith-diffuse sera, these were made as type A. When second strain was diffused type growth in the SSA containing anti-Smith-diffuse strain sera, heat-killed vaccine was made and was injected into a rabbit for the preparation of the antisera. The second strain showed compact type growth only in the SSA containing homologous strain antisera. This type of representative strain was the strain NS58D and strains represented similar serological characteristics were made as type B. With the same procedure, when the third strain was diffuse type growth in the SSA containing anti-type A and/or anti-type B, heat-killed vaccine was made for the preparation of antisera. This strain produced compact type colonies only in the SSA containing homologous strain antisera. This type of representative strain was the strain NS41D and the strains represented similar serological characteristics were made as type C. Similarly, strain of type D which representative strain was the strain NS68D, was determined. Regarding the type A, B, C and strains, serological heterogeneities were further elucidated by the absorption tests of the converting activity, diffuse to compact type growths in the SSA containing antisera, by using each type of whole cell. Further, converting activity was regarded as specific anti-capsular antibody to each strain. With the procedure, new types, type B, C and were successfully isolated, however, further types strains, type E, F and G and so on were involved in this invention when these could be isolated. These different encapsulated *S. aureus* strains were cultured in the following media. Ten gms peptone was dissolved in 50 ml of 3% NaCl solution at 4° C. for two days. To this dialysate, 50 ml of pH 7.2, 1.0 mol of phosphate buffer ($Na_2HPO_4$ and $KH_2PO_4$), 10.0 gms mannit, 2.0 gms lactose, 5.0 gms $K_2HPO_4$ and 5.0 gms casamino acid were added and autoclaved at 121° C. for 15 minutes. This media was designated as Modified 110. Encapsulated *S. aureus* strain, e.g., Smith-diffuse strain was cultured in 300 ml of Modified 110 broth at 37° C. for overnight. Five ml was inoculated into a Petri dish containing approximately 20 ml of the Modified 110 media which contained 1.5% agar and cultured at 37° C. for overnight. The organisms were scraped off and were treated with sonic oscillator (10 KC) for 5 minutes. Sonic oscillation did not cause a decrease in living cell numbers. The solution was centrifuged at 7,000×g for 20 minutes and the supernate was transfered into a dialysis bag. The supernate was concentrated using polyethylene glycol, MW=6,000, at 4° C. overnight. The concentrated material was dissolved at a pH of 7.2, M/15 mol phosphate buffer, then 50 mcg/ml and 10 mcg/ml of ribonuclease and deoxyribonuclease respectively were added. The thus treated materials were kept at 37° C. in a water bath for 30 minutes. The same volume of chloroform containing n-butanol at the ratio of 1:5 was added thereto. The mixture was shaken approximately for 30 minutes and the top layer was removed after centrifugation at 1,000×g for 15 minutes. This procedure was repeated until the white colored middle layer disappeared. The top layer was then dialyzed against a pH of 7.2, M/15 mol phosphate buffer at 4° C. for overnight. Then, 3% sodium acetate, pH 6.3, was added to the thus obtained material to a final concentration, and maintained at 4° C. for overnight after the addition of 5 volume of 95% ethyl alcohol thereto. The resulting precipitate was recovered by centrifugation at 1,000×g for 15 minutes and then was redissolved in 3% sodium acetate. Alcohol treatment of the precipitate was repeated 3 times, and the, 5 volumes of acetone were added thereto. The mixture was agitated and the supernate was discarded after centrifugation at 1,000×g for 5 minutes. Ethyl ether was added to the precipitate and then dried. The resulting material was a capsular polysaccharide and the preparation was performed for each type strain. These polysaccharides show different serological characteristics for agar diffusion tests, mouse protection experiments and absorption tests of the converting activity of antisera. The minimum protection does of these capsular polysaccharides for 15 to 20 gms mice was found to be 5 mcg per mouse.

Example 2

Strain SMU 76 of *S. epidermidis* was cultured and a cell suspension prepared in physiological saline having a 1.0 O.D. of turbidity. This was heated at 121° C. for 15 minutes to produce a "heat-killed" vaccine. One ml of this heat-killed vaccine was injected intravenously into a rabbit, weighing 2 kg, for a period of three successive days a week. Ten days after a regimen of 3 to 5 week injections, antibody activity of the rabbit hyperimmune serum was measured as follows:

0.5 ml of immune rabbit serum was heated at 56° C. for 30 minutes, then a 1:2 serial dilution was made using 0.85% NaCl solution. One tenth ml of the heat-killed vaccine was added thereto, mixed well, left at 37° C. water bath for 2 hours and then further incubated at 4° C. for overnight. A bacterial agglutination titer was measured. When maximal serum dilution, showing bacterial agglutination, was less than 1:128, further injections of the vaccine were administered.

With strains SMU 76 or SMU 76-like organisms thus obtained, protective activity against challenge with these strains could be observed by both active and passive immunization in mice, showing serological homogeneity with each of the other strains. Also, it has already been elucidated that this phenomenon was regarded as being due to specific substances within the capsule. Further, the capsular structure of these strains could be demonstrated by electronmicroscopy.

Extraction of Capsular Polysaccharide

Ten grams of a peptone were added to 50 ml of 3% NaCl solution. After dissolving the peptone by use of heat, the solution was transferred into a dialysis bag and dialyzed against 950 ml of 3% NaCl solution at 4° C. for two nights. To this dialysate, 50 ml of 1.0 M phosphate buffered solution, pH 7.2 ($Na_2HPO_4$, $KH_2PO_4$), 10 g mannit, 2.0 g lactose, 5.0 g $K_2HPO_4$ were added. The mixture was autoclaved at 155° C. for 10 minutes. This medium was tentatively designated as Modifie 110 broth. Strain SMU 76 was cultured in 300 ml of Modified 110 broth at 37° C. for 24 hours. To 20 ml of Modified 110 broth containing 1.5% agar, 5 ml of the above growing cell suspension was poured. The solution was left to stand at 37° C. for 24 hours, afterwhich the organisms were scraped off. These organisms were treated with a 10 KC sonic oscillator for 5 minutes. With this treatment, no diminishment of viable cell number was observed. These were centrifuged at 7,000×g for 20 minutes an the supernatant was transfered into a dialysis bag. This was centrifuged with polyethylene glycol (MW=6,000) at 4° C., dialyzed against a 1/15 molar phosphate buffered solution and the solution precipitated by the addition of ethyl alcohol. The precipitate was redissolved in a phosphate buffered solution, a similar volume of chloroform and n-butanol, at a ratio of 5:1. These were mixed well using a homogeneizer. The white precipitate obtained by this treatment was removed using centrifugation, and the treatment was repeated until no more precipitate appeared. After deproteonization, sodium citrate was added to the water soluble layer at 3% in final concentration. A further 5 volumes of ethyl alcohol was added and the resulting precipitate was recovered by centrifugation.

An appropriate volume of acetone was added to the precipitate, mixed well, then the supernatant obtained by centrifugation was discarded. Subsequently, ether was added to the precipitate and a similar procedure was performed as mentioned above. Finally, the precipitate was dried in vacuo. The desired polysaccharide substance was thus obtained.

When using a SMU 76-like strain instead of SMU-76, a polysaccharide substance was still similarly isolated using the above procedure.

It was then confirmed that the serological properties of the polysaccharide substance thus obtained was different from those of capsular type A, B, C and D strains of *S. aureus*.

With active immunization of 10 mcg of this polysaccharide substance in 15 to 20 gms of mice, the animals protected against challenge infection with SMU 76 or SMU 76-like strains. Also, minimal quantitative activity of hyperimmune rabbit serum prepared with SMU 76 or SMU 76-like strains protecting in mice against challenge infection with $10^9$ organisms of SMU 76 or SMU 76-like strains could be completely absorbed with 5 mg of these organisms. However, mice immunized with polysaccharide from unencapsulated strains of *S. epidermidis* by the same method as above, were not immunized against challenge infection. Also, it was noted that mouse protective activity of hyperimmune rabbit serum prepared with SMU 76 or SMU 76-like strains were not absorbed with unencapsulated strains of *S. epidermidis*.

Example 3

White cell counts on milk from each of four teats from two groups of cows, one group being vaccinated against infection and the other a control group. The front pair of teats share a lymphatic system, making the probability of a second front teat becoming infected given that the first is infected about 0.80. The same is true for the rear pair. A low probability (about 0.4) exists of a front to rear infection.

Measurements were taken as follows:

Ten days after the initial sample the animal was vaccinated. One week following the injection, the second sample was taken. One week following the second sample, a third sample was taken and a second injection was given. The fourth and fifth samples were taken 30 and 60 days, respectively, following the second injection.

A herd of 196 cows at the Reidsville State Prison were treated as above described with the vaccine of Example 2. It was found that:

1. The percent of bovine Staphylococcal infection decreased 50% within one week following the second injection while the level of infection in the control group remained approximately constant, and this condition prevailed for thirty days.

2. One week after the second injection, the level of streptococcus infection in the vaccinated group dropped by approximately 45% while the level of infection of the control group remained constant and this condition prevailed for thirty days after the second injection except for a slowly rising level of infection in the vaccinated group. Thirty days following the second injection the infection level of the vaccinated group had risen from a low of 45% up to 60% of its previous level while the infection rate in the control group remained essentially constant.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A method of producing a heat-killed vaccine from a strain of S. epidermidis ATCC 31432 which comprises:
   a. culturing said S. epidermidis strain in a culture broth;
   b. isolating polysaccharide encapsulated S. epidermidis from said broth; and
   c. heat inactivating said polysaccharide encapsulated S. epidermidis and recovering said heat-killed vaccine.

2. The method of claim 1, wherein said heat inactivated strain is injected into a host animal to induce an antibody response and the antibody containing serum from said host is recovered.

3. A method of producing a polysaccharide vaccine characterized by active immunization activity to challenge infection, which comprises:
   a. culturing an S. epidermidis strain ATCC 31432 in a culture broth;
   b. isolating polysaccharide encapsulated epidermidis from said broth; and
   c. subjecting said cells to sonic oscillation and deproteonization and recovery of said polysaccharide.

4. The vaccine produced by the method of claim 1.

5. The vaccine produced by the method of claim 2.

6. The vaccine produced by the method of claim 3.

7. A method for immunizing bovines against challenge infection which comprises administering to said animal an amount of capsular polysaccharide derived from S. epidermidis ATCC 31432 sufficient to elicit an immunizing antibody response.

8. A method for immunizing bovines against challenge infection which comprises administering to said animal an amount of a heat inactivated encapsulated S. epidermidis ATCC 31432 sufficient to elicit an immunizing antibody response.

* * * * *